(12) United States Patent
Avshalumov

(10) Patent No.: US 11,504,504 B2
(45) Date of Patent: Nov. 22, 2022

(54) SYSTEMS AND METHODS FOR EXPANDING A CATHETER

(71) Applicant: Semen Avshalumov, Staten Island, NY (US)

(72) Inventor: Semen Avshalumov, Staten Island, NY (US)

( * ) Notice: Subject to any disclaimer, the term of this patent is extended or adjusted under 35 U.S.C. 154(b) by 0 days.

(21) Appl. No.: 17/082,346

(22) Filed: Oct. 28, 2020

(65) Prior Publication Data
US 2021/0121665 A1    Apr. 29, 2021

Related U.S. Application Data

(60) Provisional application No. 62/926,916, filed on Oct. 28, 2019.

(51) Int. Cl.
*A61M 25/06*     (2006.01)
*A61M 29/00*     (2006.01)
*A61M 25/09*     (2006.01)

(52) U.S. Cl.
CPC .... *A61M 25/0606* (2013.01); *A61M 25/0631* (2013.01); *A61M 25/09* (2013.01); *A61M 29/00* (2013.01)

(58) Field of Classification Search
CPC ............ A61M 25/606; A61M 25/0606; A61M 25/0662; A61M 25/0631; A61M 25/09; A61M 25/00; A61M 2025/0024; A61M 29/00
See application file for complete search history.

(56) References Cited

U.S. PATENT DOCUMENTS

| | | | | |
|---|---|---|---|---|
| 5,176,659 A | * | 1/1993 | Mancini | A61M 25/0023 604/164.1 |
| 2004/0030319 A1 | * | 2/2004 | Korkor | A61M 25/0662 604/506 |
| 2004/0087913 A1 | * | 5/2004 | Rogers | A61M 25/0631 604/263 |
| 2016/0213882 A1 | * | 7/2016 | Fitterer | A61M 29/02 |
| 2020/0094025 A1 | * | 3/2020 | Wisman | A61M 25/0097 |

OTHER PUBLICATIONS

Unknown, What IV needle size should I use?, Nov. 23, 2015, Infusion Nurse Blog, p. 2 (Year: 2015).*

* cited by examiner

*Primary Examiner* — Bhisma Mehta
*Assistant Examiner* — Phoebe Anne Staton
(74) *Attorney, Agent, or Firm* — Jon E. Gordon; Haug Partners LLP

(57) ABSTRACT

Embodiments of the present invention provide for a catheterization system and related methods. The systems and methods provide for the initial placement of a smaller diameter catheter within a patient, the catheter being expandable to a larger diameter by the implementation of a dilator, wherein the dilator is configured to contact and expand a lumen of the catheter as it is inserted therethrough.

13 Claims, 4 Drawing Sheets

SYSTEMS AND METHODS FOR EXPANDING A CATHETER

CROSS-REFERENCE TO RELATED APPLICATION

This application claims the benefit of U.S. Provisional Patent Application No. 62/926,916, which was filed on Oct. 28, 2019 and is incorporated by reference in its entirety.

BACKGROUND OF THE INVENTION

Intravenous (IV) catheters are used widely in the hospital setting and may be used for diagnostic or therapeutic purposes. Such catheters are invaluable for patients in an inpatient setting. Generally, IV catheters are utilized to introduce fluids and medication into the body. They can be placed by physicians, nurses, physician assistants, students, etc. They are also used in a vast array of medical specialties including internal medicine, surgery, anesthesia, obstetrics, pediatrics, emergency medicine, and in an Intensive Care Unit (ICU) setting. IV catheters are necessary for the infusion of IV fluids, medications, and blood products. Therefore, they are both essential and can be life-saving.

IV catheters are produced in differed sizes and gauges. The larger the catheter, the more useful it proves itself to be. Larger catheters are typically used to rapidly introduce large amounts of fluid into the body. For example, if a patient is hypovolemic and in shock or at risk of shock, the IV catheter is inserted into a patient's blood vessel and a large volume of fluid is rapidly delivered through the catheter. In order to facilitate rapid, high-volume infusion of fluid into a blood vessel, the catheter should have an outer diameter equal to the maximum inside diameter of the blood vessel. However, such catheters are often difficult and/or impractical to insert into the blood vessel due to their large size.

Thus, in many patients placing a large IV catheter is very challenging and sometimes impossible. Additionally, in times of trauma, the circulatory system of a patient will contract to reduce blood flow. As a result, it is even more difficult to insert a catheter intravenously to provide necessary medication to the patient. In those instances, medical personnel are often forced to use a catheter with a large gauge (i.e., smaller outer diameter) than necessary in order to facilitate the insertion of the IV catheter into a contracted vein. However, small catheters have limited use because they can only deliver limited amounts of medication. For instance, a trauma patient cannot receive a blood transfusion through a small catheter. As such, medical personnel must place a central line, which is significantly more invasive and carries a higher risk for complications. Alternatively, medical personnel may have to make repeated attempts to insert a larger catheter tube, which results in a delay in providing medication and can cause damage to the patient's skin and veins.

Therefore, there exists a need in the art for a catheter whose gauge can be modified after placement. Such a catheter would provide the advantage of easier placement while also allowing for subsequent infusion of larger quantities of fluid without the need for replacement with a larger diameter catheter. For example, if a patient has small veins a small IV catheter could be placed, which could subsequently be expanded to have a larger diameter. This procedure advantageously achieves the minimally invasive benefits of small IV catheters, but allows for the delivery of rapid amounts of fluid to the patient if it becomes necessary without having to place a separate, larger catheter. Such an invention prevents the delay of the administration of medication as well as damage to skin and veins that current procedures require. Although it has been suggested to employ expandable drainage tubes for other medical procedures, the current art lacks the ability to increase the fluid carrying capacity of an intravenous catheter.

SUMMARY OF THE INVENTION

Various illustrative embodiments of the present disclosure provide a catheterization system and related methods. In accordance with an aspect of an illustrative embodiment of the present disclosure, the catheterization system is configured to place a catheter within a vein of a patient. Once placed, a dilator is configured to be inserted into the catheter thereby increasing its diameter and reducing its gauge.

According to embodiments of the present disclosure, the catheterization system includes a housing, a needle, a catheter, and a dilator. The needle may be an insertion needle having a proximal end, a distal end, and a shaft defining a lumen extending therebetween. The distal end may include a sharp distal tip. The needle may include or otherwise be associated with a needle holder. The needle holder is configured to advance and retract the needle in relation to the catheter.

The catheter may include a proximal end, a distal end, and a shaft defining a lumen extending therebetween. The lumen may be used to infuse fluids into a patient as well as remove fluid from a patient. The catheter may be made from a material that is deformable such that the diameter of the lumen may be increased (e.g., the catheter lumen may be expanded).

According to embodiments, the dilator may include a proximal end, a distal end, and a shaft extending therebetween. The distal end may include at least a portion with an increased diameter relative to the shaft. The portion may be shaped such that the diameter increases from a first diameter to a second diameter. The first diameter may be selected to be the diameter of the shaft while the second diameter may be selected to correspond to a diameter that is larger than the diameter of the lumen of the catheter, for example, the approximate diameter of a patient's vein or the approximate diameter of a lower gauge catheter. The change in diameter along at least a portion of the distal end may create a curved profile. The shape may be, for example, a tear-drop shape, a spherical shape, or an elliptical shape. The change in diameter may also take a variety of other shapes, and the present disclosure is not limited to curved shapes. The dilator may include or otherwise be associated with a dilator holder. The dilator holder is configured to advance and retract the dilator in relation to the catheter. Alternatively (or additionally), the dilator may be associated with a guide wire to guide movement of the dilator.

According to embodiments, in an initial configuration the housing is configured to house the needle and the dilator and is further configured to be releasably connected to the catheter. In alternative embodiments, the dilator is kept separate from the housing, the needle, and the catheter in the initial configuration. In the initial configuration, the insertion needle is at least partially surrounded by the catheter. The housing may further include a locking mechanism to lock the needle and/or dilator within the housing after the catheter has been placed within a patient.

According to aspects of the present disclosure, methods of using the catheterization system include placing the housing adjacent a skin surface of a patient, piercing the skin of the patient with the sharp distal tip of the insertion needle such that the distal tip is located within a body lumen, advancing the catheter into the body lumen, removing the needle, inserting a dilator into the catheter such that the diameter of the catheter is increased, removing the dilator, and separating the housing from the catheter.

According to embodiments, the distal end of the dilator is configured to contact and expand the lumen of the catheter as it is inserted therethrough. According to embodiments, the dilator is configured to expand the lumen of the catheter, such that the gauge of the catheter is reduced by at least one size. According to a preferred embodiment, the dilator is configured to expand the lumen of the catheter, such that the gauge of the catheter is reduced by more than one size. According to one preferred embodiment, when a 24 gauge catheter (i.e., a catheter with an external diameter of 0.7 mm) is implemented, the dilator is configured to increase the external diameter such that the catheter is converted to a 20 gauge (i.e., a catheter with an external diameter of 1.1 mm) catheter. Differing starting gauges and converted gauges of the catheter are within the scope of the present disclosure.

The catheterization system and related methods of the present disclosure allow for the initial placement within a patient of a smaller diameter catheter, which can subsequently be expanded to a larger diameter. This advantageously allows for easier catheter placement, since a smaller diameter catheter is initially used. Additionally, such systems and methods obviate the need to replace a smaller catheter with a larger one when the need arises, for example, when higher fluid flow rates are necessary. This also reduces the need for a central line to be placed, since the expanded catheter can accommodate the needs that the central line would be used for.

BRIEF DESCRIPTION OF THE DRAWINGS

The following description is given as an example, and is not intended to limit the scope of the invention to the disclosed details, is made in conjunction with the accompanying drawings, wherein.

DETAILED DESCRIPTION

Figure 1:
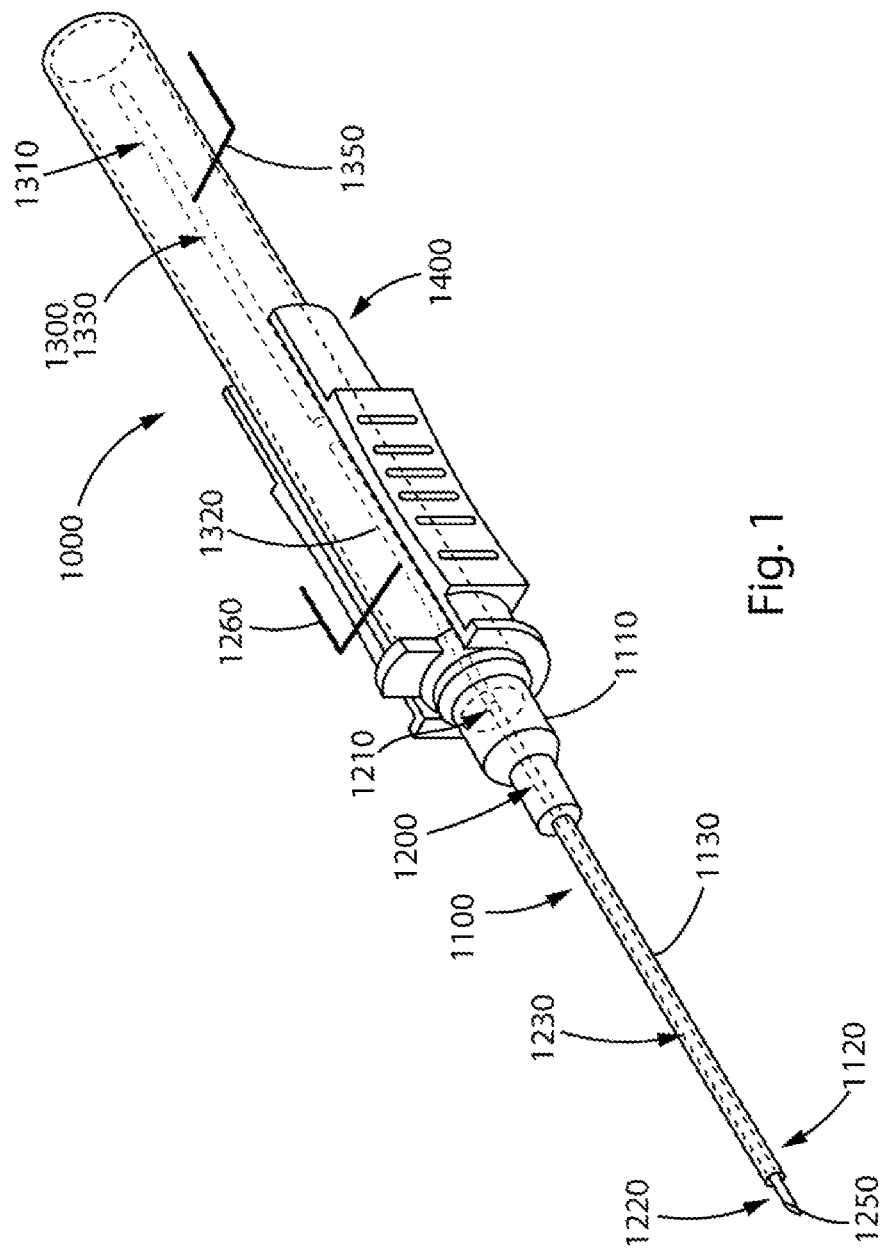
FIG. 1 illustrates a catheterization system in an initial configuration according to an embodiment of the invention.

FIG. 1 illustrates a catheterization system 1000 in an initial configuration, according to an embodiment of the present invention. The catheterization system 1000 includes a needle 1200, a catheter 1100, a housing 1400, and a dilator 1300. The housing 1400 is configured to house at least a portion of needle 1200 and dilator 1300, and be coupled to catheter 1100.

In the initial configuration, the components of catheterization system 1000 are oriented such that a user of the device can provide initial placement of the catheter 1100 within a blood vessel of a patient. For example, catheter 1100 includes a proximal end 1110 and a distal end 1120. The proximal end 1110 and distal end 1120 define a shaft 1130 that includes a lumen. Proximal end 1110 may be releasably attached to a distal end of housing 1400. Needle 1200 may be an insertion needle having a proximal end 1210 and a distal end 1220 terminating in a sharp distal tip 1250. The proximal end 1210 and distal end 1220 define a shaft 1230 that includes a lumen. The needle may include or otherwise be associated with a needle holder 1260. Needle 1200 is generally housed within a lumen of catheter 1100 and within housing 1400 with the exception of the sharp distal tip 1250, which protrudes beyond distal end 1120 of catheter 1100. In this way, a user of the device is able to pierce the skin of a patient with the distal tip 1250 thereby placing the needle 1200 and catheter 1100 within a blood vessel of a patient.

Dilator 1300 may include a proximal end 1310, a distal end 1320, and a shaft 1330 extending therebetween. The dilator 1300 may include or otherwise be associated with a dilator holder 1350. In the initial configuration, dilator 1300 is at least partially housed within the interior of housing 1400. According to embodiments, the shaft 1330 of dilator 1300, in the initial configuration, is coaxial with the shaft 1230 of needle 1200. According to alternative embodiments, the shaft 1330 of dilator 1300 is not coaxial with the shaft 1230 of needle 1200.

The dilator may also be associated with a guide wire (not shown). According to embodiments, shaft 1330 of dilator 1300 is hollow, and a guide wire is located through the hollow shaft 1330. The guide wire may extend out of the proximal end of housing 1400 such that it is capable of being manipulated by a user.

As further illustrated by FIG. 1, needle holder 1260 and dilator holder 1350 are formed as a part of or coupled to needle 1200 and dilator 1300, respectively. These holders extend outside of housing 1400 so that a user can manipulate them, thereby moving the needle 1200 and dilator 1300, which will be described in more detail below. Housing 1400 may include openings, such as slots, along its length to accommodate and limit axial movement of the holders. Housing 1400 may also include a locking mechanism 1410 that is configured to lock or otherwise prevent movement of the needle 1200 and/or dilator 1300.

Figure 4:
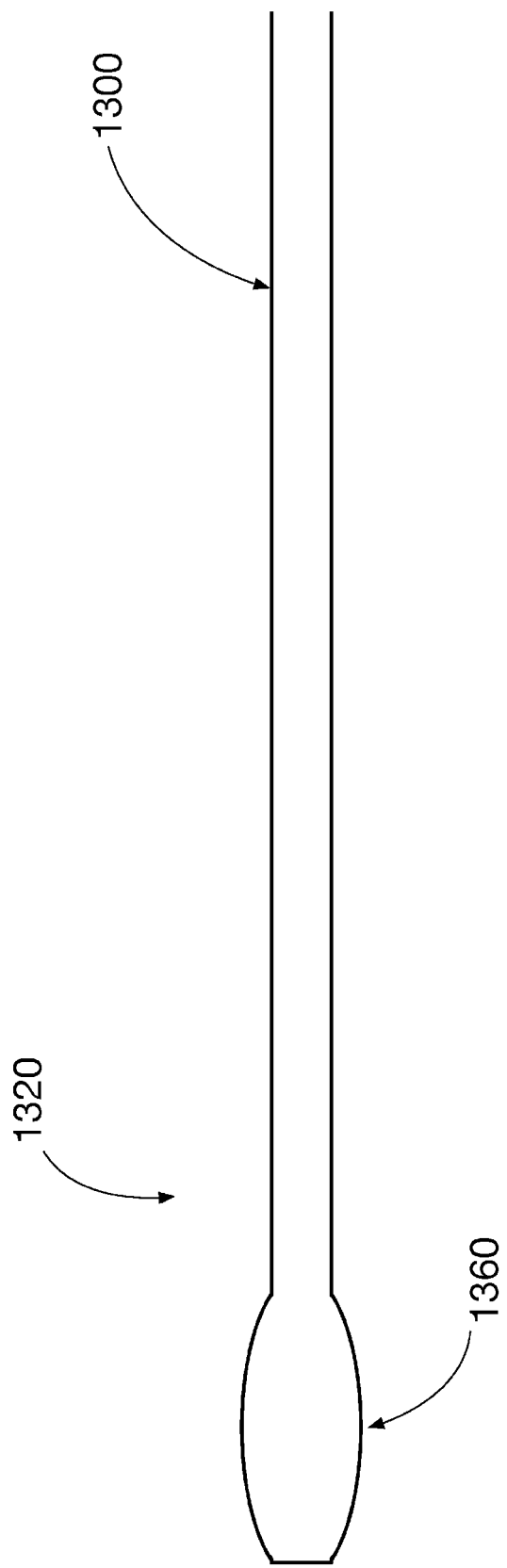
FIG. 4 illustrates part of a dilator according to an embodiment of the invention.

FIG. 4 illustrates in more detail a distal end 1320 of a dilator 1300 according to an embodiment of the invention. As depicted, the distal end 1320 of the dilator 1300 includes a portion 1360 shaped such that the diameter increases from a first diameter that is selected to be the diameter of the shaft 1330 to a second diameter, which may, e.g., be larger than the diameter of the lumen of the catheter. As depicted, this portion 1360 has an elliptical profile.

Figure 2:
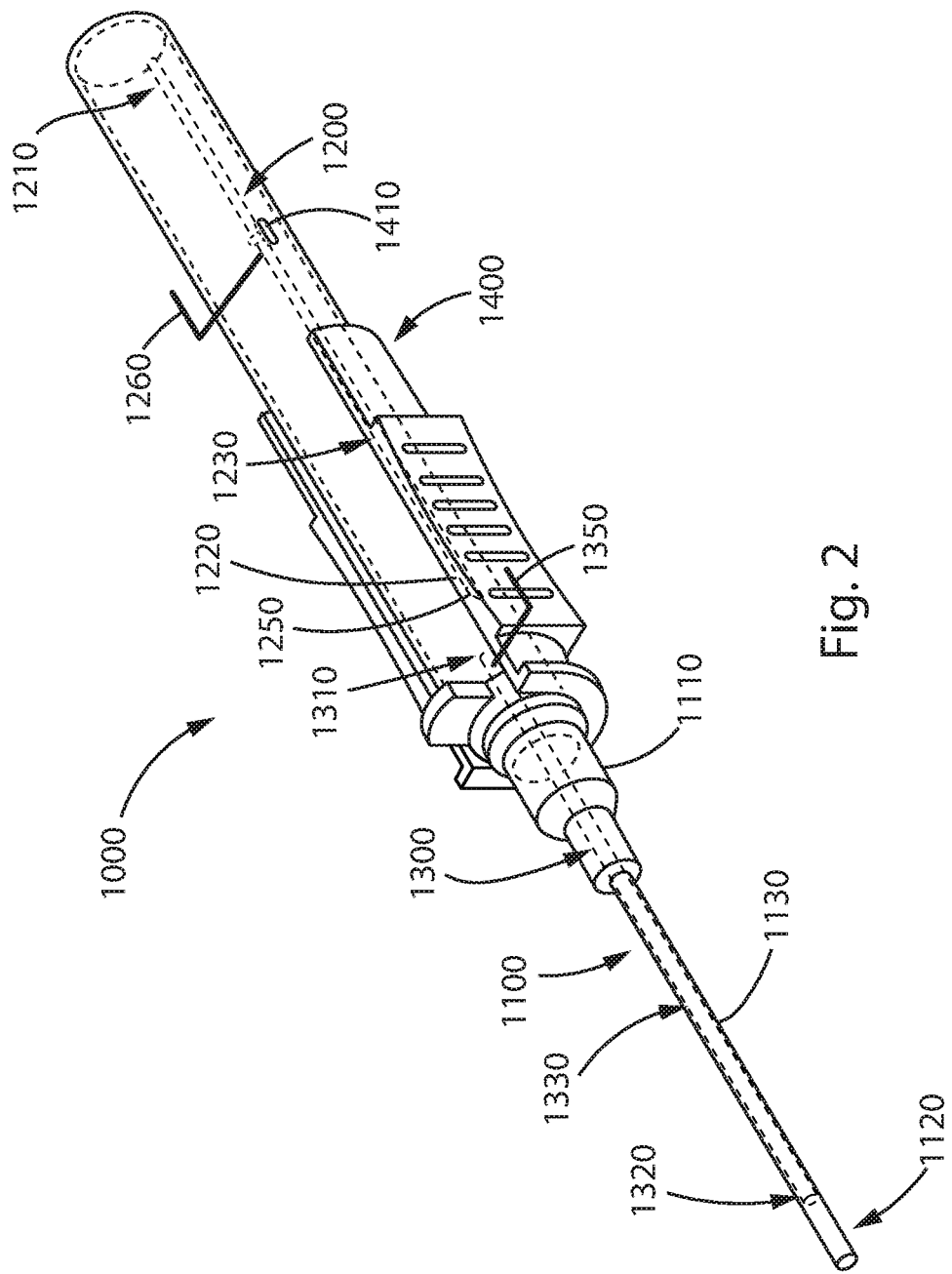
FIG. 2 illustrates a catheterization system in a catheter expansion configuration according to an embodiment of the invention.

The distal end 1320 of dilator 1300 may include at least a portion with an increased diameter relative to the shaft 1330 (not shown in FIGS. 1 and 2). The portion may be shaped such that the diameter increases from a first diameter to a second diameter. The first diameter may be selected to be the diameter of the shaft while the second diameter may be selected to correspond to a diameter that is larger than the diameter of the lumen of the catheter (e.g., a diameter corresponding to a lower gauge catheter or the approximate diameter of the of the blood vessel). The change in diameter along at least a portion of the distal end may create a curved profile. The shape may be, for example, a tear-drop shape, a spherical shape, or an elliptical shape. The change in diameter may also take a variety of other shapes, and the present disclosure is not limited to curved shapes.

FIG. 2 illustrates a catheterization system 1000 in a catheter expansion configuration, according to an embodiment of the present invention. In the catheter expansion configuration of FIG. 2, needle 1200 has been retracted into the housing 1400 by proximal movement of needle holder 1260 relative to housing 1400. Once the needle 1200 is located within housing 1400, locking mechanism 1410 may lock the needle so that it can no longer move in relation to the housing. This ensures that the distal tip 1250 is covered, preventing accidental exposure of the tip after the catheter has been placed in the patient and the housing has been removed.

In the catheter expansion configuration, and after the needle 1200 is no longer located within the catheter, dilator 1300 is advanced into the lumen of catheter 1100, for example, by way of distal movement of dilator holder 1350 relative to housing 1400. Since distal end 1320 of dilator 1300 includes at least a portion with an increased diameter that is larger than the diameter of the lumen of the catheter, the catheter is expanded at the location of the distal end 1320. The dilator 1300 may be advanced through and retracted from the lumen of catheter 1100 one or more times in order to ensure that the catheter lumen has expanded to the outer diameter of distal end 1320. According to certain embodiments, the guide wire may be implemented to help guide movement of the dilator through the catheter. According to further embodiments, the guide wire may be directly used to move the dilator through the catheter, thereby obviating the need for dilator holder 1350.

According to embodiments, the catheter 1200 is made from a material that is sufficiently stretchable such that when the dilator is passed through the catheter stretches, but does not constrict back to its original size. The material must also be rigid enough to maintain its placement within the blood vessel and carry out the necessary functions (e.g., the functions of an intravenous catheter). Additionally, dilator 1300 is made from a material that is sufficiently rigid enough to stretch the catheter as it is advanced and/or retracted therethrough.

According to an illustrative embodiment, the dilator 1300 is configured to expand the lumen of the catheter 1100, such that the gauge of the catheter 1100 is reduced by more than one size. For example, when a 24 gauge catheter (i.e., a catheter with an external diameter of 0.7 mm) is implemented, the dilator 1300 is configured to increase the external diameter such that the catheter is converted to a 20 gauge catheter (i.e., a catheter with an external diameter of 1.1 mm). Differing starting gauges and converted gauges of the catheter, as well as the outer diameter of distal end 1320 are within the scope of the present disclosure.

Figure 3:
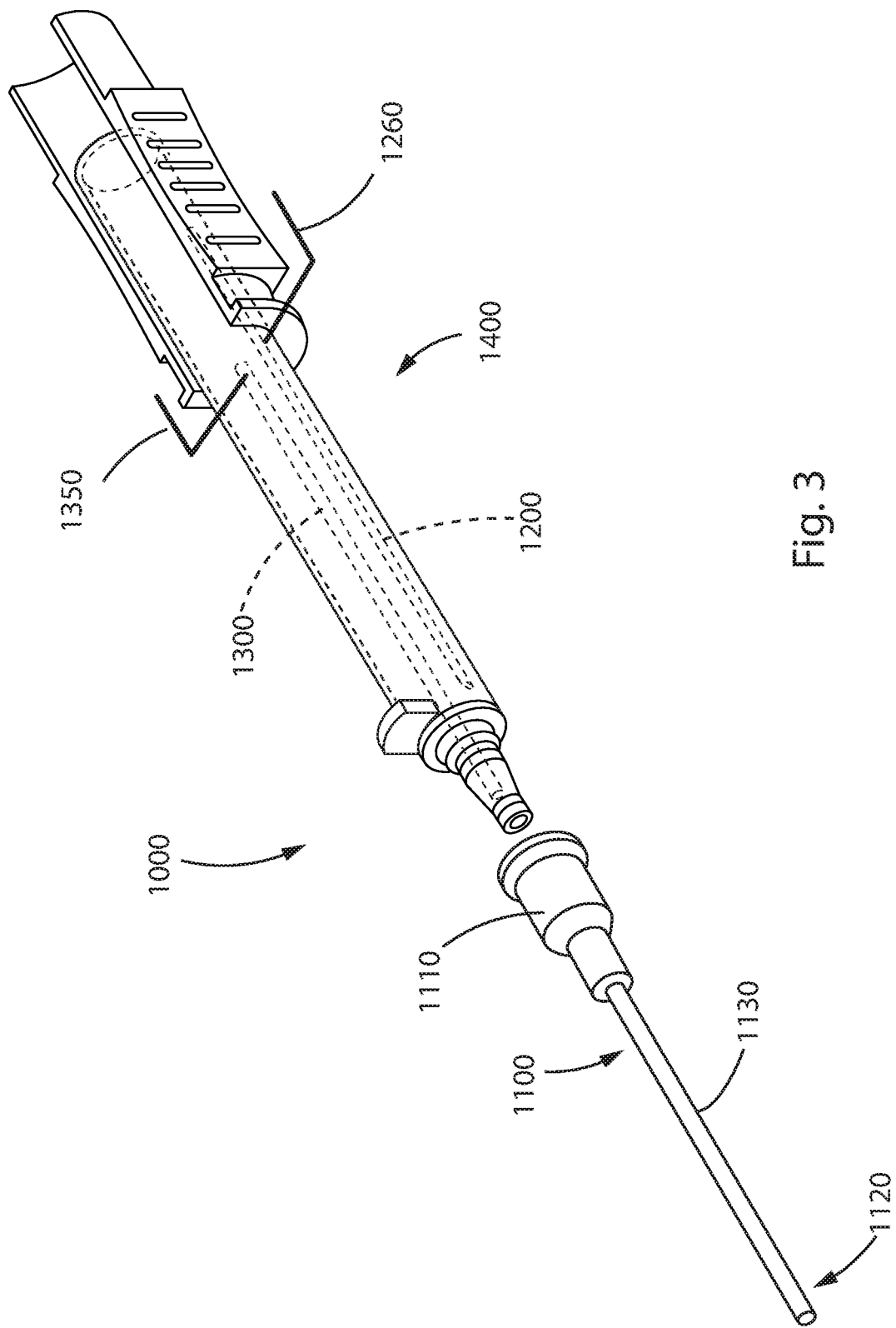
FIG. 3 illustrates a catheterization system after the catheter has been separated from the catheterization system according to an embodiment of the invention.

After the catheter 1100 has been placed within the blood vessel, and after the dilator 1300 has been passed through the catheter 1100 to expand its lumen, the dilator 1300 can be fully retracted into the housing 1400 and the catheter 1100 can be separated from the housing 1400, as illustrated by FIG. 3. In this way, once the catheter 1100 has been expanded to a desired gauge, the housing 1400, which encases the dilator 1300 and needle 1200, can be easily and quickly removed from catheter 1100. The catheter 1100 can then be connected to, for example, a fluid delivery system (e.g., an IV bag) or other medical devices configured to infuse or withdraw fluids from the patient.

Methods of using the catheterization system 1000 will now be described. According to an illustrative embodiment, the method includes placing the housing 1400 adjacent a skin surface of a patient when the catheterization system 1000 is in the initial configuration of FIG. 1. Once placed, the needle 1200 is advanced in order to pierce the skin of the patient with the sharp distal tip 1250, such that the needle 1200 is at least partially located within a body lumen. The needle 1200 and catheter 1100 are then advanced until the distal end 1120 of catheter 1110 is properly placed in the body lumen. The needle 1200 is then withdrawn from the body lumen and the catheter and into the housing 1400 by proximally moving the needle holder 1260. Once the needle 1200 is withdrawn, dilator 1300 is inserted into the catheter 1100 such that the diameter of the catheter 1100 is increased. Subsequently, the dilator is withdrawn into the housing 1400 by proximally moving the dilator holder 1350. The final step includes separating the catheter 1100 from the housing.

According to certain embodiments, the catheter's 1100 diameter is expanded prior to the separation of the housing 1400 from the catheter 1100. According to alternative embodiments, the catheter is initially placed within the body lumen using the catheterization system 1000 and the housing 1400 is removed without catheter expansion. Subsequently, when a larger diameter catheter is needed the housing 1400 (or a new housing 1400) may be reattached (or newly attached) and the dilator can be advanced into the catheter 1100 in order to expand its diameter.

The presently described catheterization system and related method allows for the initial placement of a smaller diameter catheter within a patient, which is subsequently expanded to a larger diameter. This advantageously allows for easier catheter placement, since a smaller diameter catheter is initially used. Additionally, such systems and methods obviate the need to replace a smaller catheter with a larger one when the need arises, for example, when higher fluid flow rates are necessary. This also reduces the need for a central line to be placed, since the expanded catheter can accommodate the needs that the central line would be used for.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Although illustrative embodiments of the invention have been described in detail herein with reference to the accompanying drawings, it is to be understood that the invention is not limited to those precise embodiments, and that various changes and modifications can be effected therein by one skilled in the art without departing from the scope and spirit of the invention.

The invention claimed is:

1. A catheterization system, the system comprising:
a housing, a needle, a catheter, and a dilator, wherein:
the needle includes a first proximal end, a first distal end, and a first shaft defining a first lumen extending between the first proximal end and the first distal end, wherein the first distal end includes a sharp distal tip;
the catheter includes a second proximal end, a second distal end, and a second shaft defining a second lumen extending between the second proximal end and the second distal end, wherein the second lumen is configured to at least one of infuse fluids into a patient and remove fluid from the patient; and
the dilator includes a third proximal end, a third distal end, and a third shaft extending between the third proximal end and the third distal end, wherein the third distal end includes a portion with an increased diameter relative to the third shaft, wherein the diameter of the portion increases from a first diameter to a second diameter; and wherein the housing is configured to house both the needle and the dilator simultaneously, and is further configured to be releasably connected to the catheter.

2. The system of claim 1, further comprising:
a needle holder, wherein the needle holder is configured to advance and retract the needle in relation to the catheter.

3. The system of claim 1, wherein the second lumen is expandable.

4. The system of claim 1, wherein the first diameter corresponds to a diameter of the third shaft and the second diameter is larger than a diameter of the second lumen.

5. The system of claim 1, further comprising:
a dilator holder, wherein the dilator holder is configured to advance and retract the dilator in relation to the catheter.

6. The system of claim 1, further comprising:
a guide wire, wherein the guide wire is configured to guide a movement of the dilator.

7. The system of claim 1, wherein, in a first configuration, the needle is at least partially surrounded by the catheter.

8. The system of claim 1, further comprising:
a locking mechanism, wherein the locking mechanism is configured to lock at least one of the needle and the dilator within the housing after the catheter has been placed within the patient.

9. The system of claim 1, wherein the third distal end is configured to contact and expand the second lumen as the second lumen is inserted through the catheter.

10. The system of claim 1, wherein the dilator is configured to expand the second lumen such that a gauge of the catheter is reduced by at least one size.

11. The system of claim 1, wherein the catheter is a 24 gauge catheter.

12. The system of claim 11, wherein the dilator is configured to increase an external diameter of the 24 gauge catheter such that the 24 gauge catheter is converted to a 20 gauge catheter.

13. A method of using a catheterization system comprising a housing, a needle, a catheter, and a dilator, the method comprising:
placing the housing adjacent a skin surface of a patient, the housing being configured to house both the needle and the dilator simultaneously;
advancing the needle out from a distal end of the housing while the dilator is retracted within the housing;
piercing the skin of the patient with a sharp distal tip of the needle such that the sharp distal tip is located within a lumen in the body of the patient;
advancing the catheter into the body lumen;
retracting the needle from the body lumen;
advancing the dilator from the distal end of the housing while the needle is retracted within the housing and then inserting the dilator into the catheter such that the diameter of the catheter is increased;
retracting the dilator from the catheter; and
separating the housing from the catheter.

\* \* \* \* \*